United States Patent [19]
Nierlich et al.

[11] Patent Number: 5,839,439
[45] Date of Patent: Nov. 24, 1998

[54] OXIMETER SENSOR WITH RIGID INNER HOUSING AND PLIABLE OVERMOLD

[75] Inventors: Steve L. Nierlich; Phillip S. Palmer, both of San Leandro; James R. Casciani, Cupertino; Mitch Levinson, Pleasanton; Stephen J. Ruskewicz, Kensington, all of Calif.

[73] Assignee: Nellcor Puritan Bennett Incorporated, Pleasanton, Calif.

[21] Appl. No.: 556,619

[22] Filed: Nov. 13, 1995

[51] Int. Cl.$^6$ .................................................. A61B 5/00
[52] U.S. Cl. .................................................. 128/633
[58] Field of Search .................... 128/632, 633, 128/642, 664–7; 356/39–41; 428/156, 160; 29/592.1, 848; 249/84, 85, 88

[56] References Cited

U.S. PATENT DOCUMENTS

| | | | |
|---|---|---|---|
| D. 250,275 | 11/1978 | Bond | D24/29 |
| 3,167,658 | 1/1965 | Richter | 250/239 |
| 3,326,207 | 6/1967 | Egan | 128/2.06 |
| 3,402,717 | 9/1968 | Doherty | 128/351 |
| 3,602,213 | 8/1971 | Howell et al. | 128/2.05 F |

(List continued on next page.)

FOREIGN PATENT DOCUMENTS

| | | |
|---|---|---|
| 671 279 | 10/1963 | Canada . |
| 0 072 185 A2 | 2/1983 | European Pat. Off. . |
| 0 094 749 A3 | 11/1983 | European Pat. Off. . |
| 0 104 619 A2 | 4/1984 | European Pat. Off. . |
| 0 135 840 A2 | 4/1985 | European Pat. Off. . |
| 0 454 886 A1 | 11/1991 | European Pat. Off. . |
| 1 909 882 | 9/1970 | Germany . |
| 43 04 693 A1 | 8/1994 | Germany . |
| 2 216 804 | 10/1989 | United Kingdom . |
| WO 88/02616 | 4/1988 | WIPO . |
| WO 89/09566 | 10/1989 | WIPO . |
| WO 90/01293 | 2/1990 | WIPO . |
| WO 90/04352 | 5/1990 | WIPO . |
| WO 91/07910 | 6/1991 | WIPO . |
| WO 91/15996 | 10/1991 | WIPO . |

OTHER PUBLICATIONS

"Care of the Fetus", Goodlin, Masson Publishing, U.S.A., Inc., 1979.
"A New Fetal Scalp Electrode", Goodlin et al., Obstetrics and Gynecology, vol. 35, No. 4, Apr. 1970.
"Systolic Time Intervals in the Fetus and Neonate", Goodlin et al., Obstetrics and Gynecology, vol. 39, No. 2, Feb. 1972.
"The fetal EEG (detection of oxygen deprivation)", Vineker, British Journal of Hospital Medicine, Nov. 1979.
"Fetal Electroencephalography Uing a New, Flexible Electrode", Weller et al., British Journal of Obstetrics and Gynaecology, Oct. 1981, vol. 88.
"General Purpose Detectors", Form No. 400 44 004, Rev. 8, Silicon Detector Corporation, Newbury Park, CA 91320.
"Silicon Diffused Pin Photodiodes SGD Series", EG&G Electro–Optics, Data Sheet D3003C–5.
"Planar Diffused Silicon Pin Photodiodes", Data Sheet 9F002, United Detector Technology, Hawthorne, CA 90250.

*Primary Examiner*—Jennifer Bahr
*Assistant Examiner*—Bryan K. Yarnell
*Attorney, Agent, or Firm*—Townsend and Townsend and Crew LLP

[57] ABSTRACT

An oximeter sensor formed with a housing made of a relatively rigid material into which the oximeter electrical components can be mounted is provided. An overmolded material, of lesser rigidity, is injection-molded over the housing to complete the sensor. In one embodiment the housing is made of plastic, such as polypropylene, and the overmolded material is an injection-molded thermal plastic elastomer, such as Santoprene™ (polypropylene with 1 micron size particles of rubber). The housing preferably contains thin portions connecting thicker portions which support the electrical and optical components. These thin portions provide natural bending portions in the final oximeter sensor. By having the thin portions near or at the central, neutral axis of the sensor, flexibility is optimized in the longitudinal direction, while the housing provides stiffness laterally.

41 Claims, 4 Drawing Sheets

U.S. PATENT DOCUMENTS

| | | | |
|---|---|---|---|
| 3,647,299 | 3/1972 | Lavalle | 356/41 |
| 3,704,706 | 12/1972 | Herczfeld et al. | 128/2 R |
| 3,769,974 | 11/1973 | Smart et al. | 128/2.05 P |
| 3,772,593 | 11/1973 | Sidhu | 324/62 R |
| 3,827,428 | 8/1974 | Hon et al. | 128/2.06 E |
| 3,841,314 | 10/1974 | Page | 128/2.05 P |
| 3,851,641 | 12/1974 | Toole | 128/2.1 Z |
| 3,983,866 | 10/1976 | Ulrich et al. | 128/2.05 P |
| 4,013,067 | 3/1977 | Kresse et al. | 128/2.05 R |
| 4,041,932 | 8/1977 | Fostick | 128/2 G |
| 4,091,803 | 5/1978 | Finder | 128/2.05 P |
| 4,136,681 | 1/1979 | Hon | 128/2 R |
| 4,244,375 | 1/1981 | Farrar et al. | 128/642 |
| 4,299,232 | 11/1981 | Zilianti | 128/642 |
| 4,324,256 | 4/1982 | Vesterager | 128/635 |
| 4,350,165 | 9/1982 | Striese | 128/640 |
| 4,370,984 | 2/1983 | Cartmell | |
| 4,396,017 | 8/1983 | Delpy et al. | 128/635 |
| 4,537,197 | 8/1985 | Hulka | 128/633 |
| 4,543,965 | 10/1985 | Pack et al. | 128/748 |
| 4,621,643 | 11/1986 | New, Jr. et al. | 128/633 |
| 4,658,825 | 4/1987 | Hochberg et al. | 128/634 |
| 4,685,464 | 8/1987 | Goldberger et al. | 128/633 |
| 4,722,730 | 2/1988 | Levy et al. | 604/118 |
| 4,808,931 | 2/1989 | Ling | 324/444 |
| 4,813,425 | 3/1989 | Malis | 128/642 |
| 4,824,242 | 4/1989 | Frick et al. | 356/41 |
| 4,825,872 | 5/1989 | Tan et al. | 128/633 |
| 4,830,014 | 5/1989 | Goodman et al. | 128/665 |
| 4,856,527 | 8/1989 | Karcher et al. | 128/634 |
| 4,859,057 | 8/1989 | Taylor et al. | 356/41 |
| 4,873,986 | 10/1989 | Wallace | 128/670 |
| 4,913,150 | 4/1990 | Cheung et al. | 128/633 |
| 4,938,218 | 7/1990 | Goodman et al. | 128/633 |
| 4,981,470 | 1/1991 | Bombeck, IV | 128/635 |
| 5,024,226 | 6/1991 | Tan | 128/633 |
| 5,025,787 | 6/1991 | Sutherland et al. | 128/642 |
| 5,080,098 | 1/1992 | Willett et al. | 128/633 |
| 5,094,240 | 3/1992 | Muz | 128/633 |
| 5,099,842 | 3/1992 | Mannheimer et al. | 128/633 |
| 5,109,849 | 5/1992 | Goodman et al. | 128/633 |
| 5,154,175 | 10/1992 | Gunther | 128/633 |
| 5,215,090 | 6/1993 | Hon et al. | 128/642 |
| 5,218,962 | 6/1993 | Mannheimer et al. | 128/633 |
| 5,228,440 | 7/1993 | Chung et al. | 128/633 |
| 5,247,932 | 9/1993 | Chung et al. | 128/633 |
| 5,361,757 | 11/1994 | Smith et al. | 128/633 |
| 5,377,675 | 1/1995 | Ruskewicz et al. | 128/634 |
| 5,411,024 | 5/1995 | Thomas et al. | 128/634 |
| 5,425,360 | 6/1995 | Nelson | 128/633 |

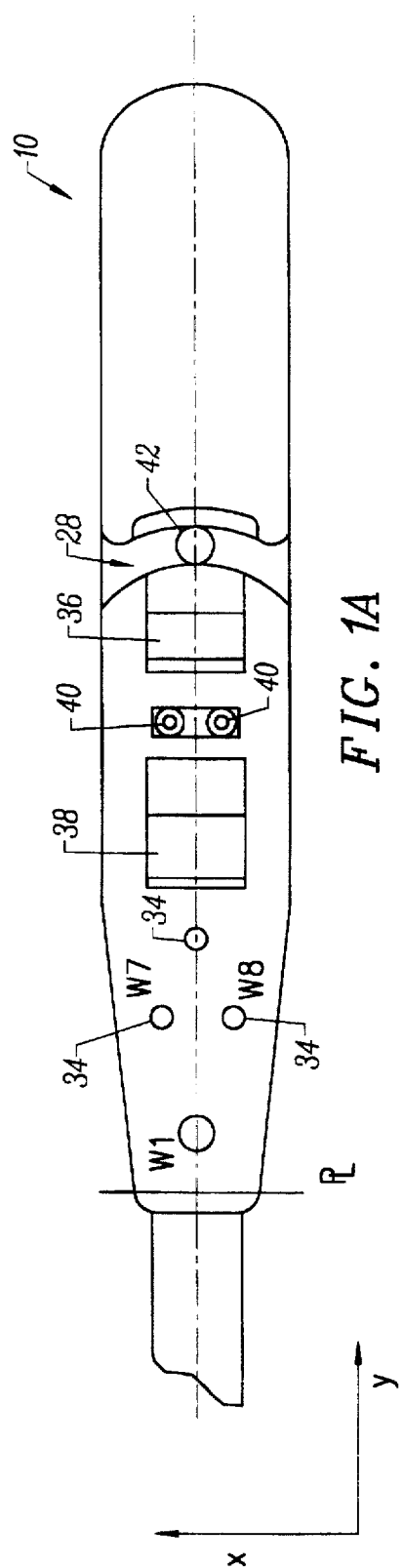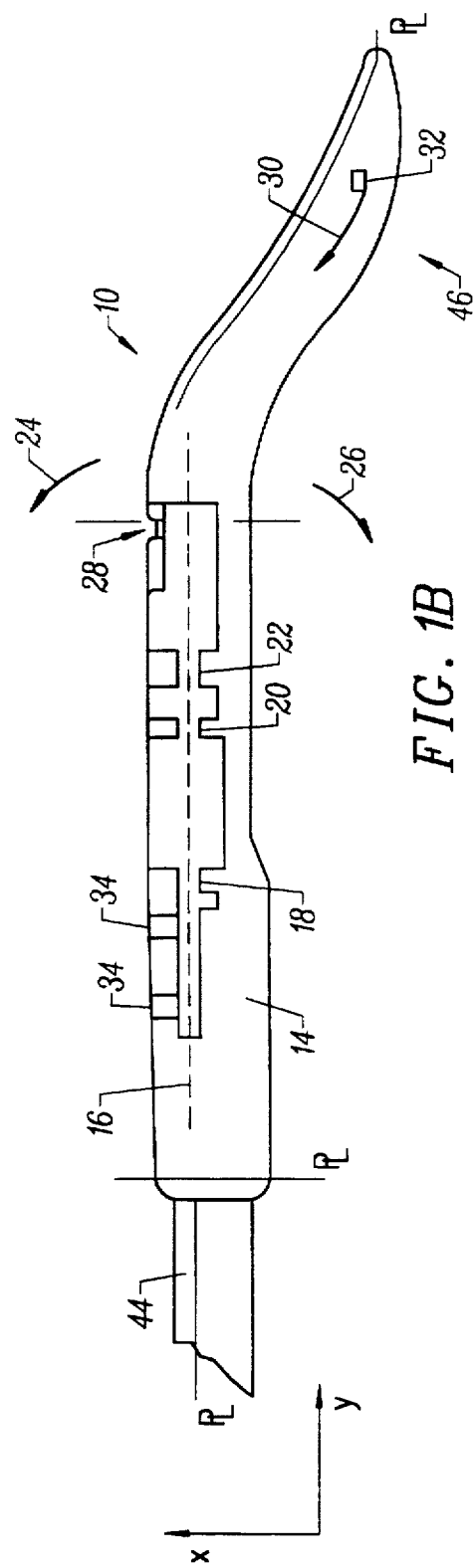
FIG. 1A
FIG. 1B

OXIMETER SENSOR WITH RIGID INNER HOUSING AND PLIABLE OVERMOLD

BACKGROUND OF THE INVENTION

The present invention relates to oximeter sensors, and in particular pliable sensors for use in fetal pulse oximetry.

An oximeter is a device for non-invasively determining the oxygen saturation of arterial blood. A pulse oximeter emits light at two different wavelengths (typically one in the red range and the other in the infrared range) through a portion of a patient's blood-perfused tissue. The red and infrared light scattered by the tissue is detected by a photodetector. The amount of light absorbed varies with the amount of oxygen in the blood, and varies differently for red and infrared light. A pulse oximeter monitor computes blood oxygen saturation based on changes in the two detected light levels between two points in time.

Fetal pulse oximeter sensors are increasingly important in determining the status of a fetus during labor. One type of fetal sensor needs to be small and pliable enough to be inserted into the uterus during labor, and bend to bias itself against the fetus. An example of such a sensor is set forth in U.S. Pat. No. 5,377,675. Such sensors have been manufactured using a silicone mold in which the electrical components are placed, with the entire apparatus being surrounded by another layer of silicone after the electrical components have been loaded. Silicone is a thermo-set process using two polymers which requires a longer cure time than injection molding. One problem with silicone is establishing an effective seal around the contact pins.

Another type of sensor, although not a fetal sensor, is shown in U.S. Pat. No. 5,425,360. This sensor design shows the use of a PVC material as an initial mold for holding the electrical components, including the light source and detector. This is then subjected to an injection molding of the same PCV material to form an overmold. The need for high temperatures is avoided by provided dovetailed-ribbing to form a mechanical bond during the overmolding process.

It is desirable to have an oximeter sensor which is pliable enough to be used as a fetal sensor, but which can be formed using a rigid housing to hold the electrical components in proper alignment.

SUMMARY OF THE INVENTION

The present invention provides an oximeter sensor formed with a housing made of a relatively rigid material into which the oximeter electrical components can be mounted. An overmolded material, of lesser rigidity, is injection-molded over the housing to complete the sensor.

In one embodiment, the housing is made of plastic, such as polypropylene, and the overmolded material is an injection-molded thermal plastic elastomer, such as Santoprene™ (polypropylene with 1 micron size particles of rubber). The housing preferably contains thin portions connecting thicker portions which support the electrical and optical components. These thin portions provide natural bending portions in the final oximeter sensor. By having the thin portions near or at the central, neutral axis of the sensor, flexibility is optimized in the longitudinal direction, while the housing provides stiffness laterally.

The invention also provides features for maintaining the housing in proper alignment during the overmolding process, including (1) a feature for mating with the mold to keep the housing from slipping longitudinally during injection-molding, (2) features for engaging the mold to ensure proper lateral alignment of the housing, and (3) features for standing off the housing from the top of the mold to ensure that it is properly covered with the appropriate depth of the overmolding material.

One embodiment of the present invention also provides features for maintaining the emitter and detector in alignment, including an enclosure within the housing for the emitter and detector to fit into. Each of the emitter and detector are covered on the backside with a lid to prevent the overmolding material from dislodging them or penetrating onto their front sides during the overmolding process. In addition, the detector is mounted in a detector block and covered by a Faraday shield before being inserted into the enclosure and covered by the lid. A front side of the openings in the housing for the detector and light emitter preferably have injection-molded clear plastic to form windows through which the light can pass during operation.

For a further understanding of the nature and advantages of the present invention, reference should be made to the following description taken in conjunction with the accompanying drawings.

BRIEF DESCRIPTION OF THE DRAWINGS

FIGS. 1A and 1B are top and side, broken-away views of a completed sensor according to the present invention;

DESCRIPTION OF THE PREFERRED EMBODIMENT

Figure 2:
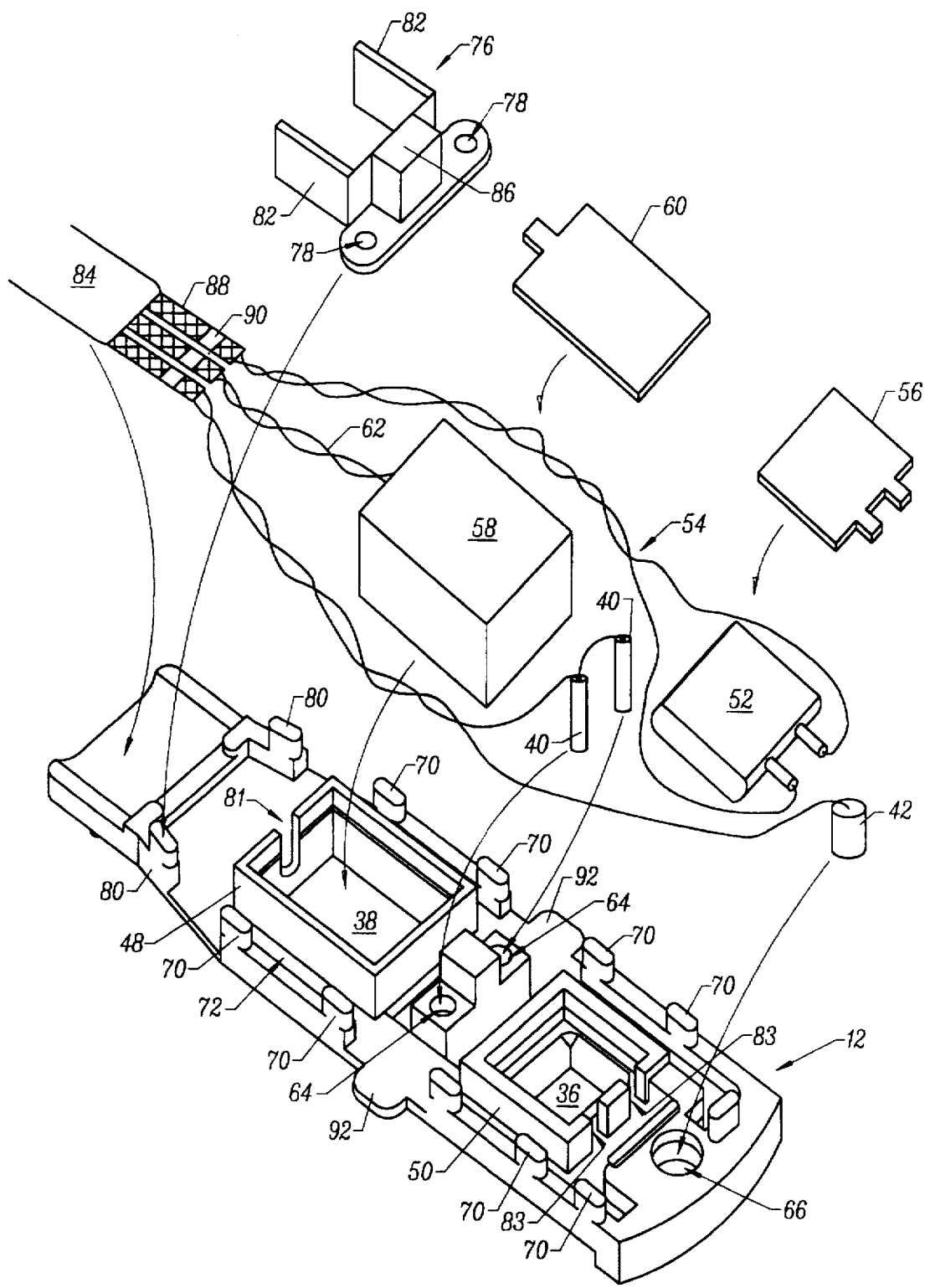
FIG. 2 is a diagram illustrating the placement of components in the rigid housing of the present invention.

FIGS. 1A and 1B show a sensor 10 according to one embodiment of the present invention. As can be seen in the cut-away view of FIG. 1B, the sensor includes an inner, relatively rigid housing 12 which holds the electronic components, and an overmolding 14 which forms the body of the sensor. Preferably, the inner housing 12 is made of polypropylene while the overmolding material 14 is preferably Santoprene™. Preferably, both the housing and the overmolding material are of the same family of materials, preferably thermoplastics, so that they will bond to each other easily. However, other materials may be used, and the housing could be, for instance, made of nylon, thermo-sets, silicones, polyester, etc. Preferably, the ratio of the rigidity of the housing material to the overmolded material is in the range of 100–3000, with the housing preferably having a modulus of elasticity in the narrower range of 50,000 to 1,000,000 psi. The overmolding material preferably has a modulus of elasticity in the range of 50 to 2000. In one embodiment, the modulus of elasticity is 130,000 for the housing and 300 psi for the overmold.

Housing 12 has thin portions along a line 16 in a longitudinal direction at points 18, 20, and 22. This allows for bending around these points in the z direction indicated by arrows 24 and 26. Line 16 is spaced away from the top surface of the sensor. Since the center portion of the sensor would undergo the least strain during bending in both directions, it is desirable to have the semi-rigid housing have these thin portions near this center portion. The bottom portion of the sensor as shown in FIG. 1B is rounded, and thus the housing line 16 is nearer the center of mass of the sensor than would appear from the figure. The portions of housing 12 which extend to the surface of the sensor are not continuous, so bending is possible between them (i.e., between the emitter and detector windows).

FIGS. 1A and 1B show two views, with FIG. 1A showing the x-y plane, and FIG. 1B showing the y-z plane. The housing 12 has its thin portions in the z direction, as seen in FIG. 1B, to give it longitudinal flexibility for bending away from the y-axis. The housing is wider in the x-direction of FIG. 1A, as can be seen more clearly in FIG. 2, to provide rigidity along the x-axis to facilitate insertion and placement of the sensor.

In one alternate embodiment, housing 12 could be made of the same or similar material as the overmold 14. In order to promote flexibility, the rigid elements, such as wires and optical and electrical parts, should be located near the neutral axis of the sensor.

The use of a semi-rigid plastic housing allows the components to be both placed and held in alignment accurately, and to be maintained in that position during a subsequent injection-molding process for adding the overmolding material 14. The overmolding material encapsulates the components and forms a water-tight seal to the plastic material around them. By using an opaque overmolding material, this creates light barriers to prevent optical shunting within the sensor body.

A number of features ensure that housing 12 is held in proper alignment during the overmolding process. A curvilinear groove 28 matches a similar protrusion in the molding housing, and keeps the housing from slipping is longitudinally during the injection-molding of the overmold material 14, which is typically done by injecting the thermoplastic material in a direction indicated by arrow 30 from an injection-molding port area 32. Alternate shapes could be used for the groove, as long as it resists the longitudinal injection pressure. Alternately, a protrusion could be used to engage a groove or hole in the mold. During the overmolding process, the Santoprene™ material fuses to the polypropylene parts of housing 12, and also fuses to a cable jacket 44, which is preferably also made of Santoprene™.

A series of three protrusions 34 act as stand-offs. Stand-offs 34 ensure that the proper distance is maintained between the housing body 12 and the top of the mold for the overmolding material 14 to ensure that the top portion of the housing 12 is covered with the injection-molded material. Alternately, the protrusions could extend from the mold to provide the stand-off function, leaving holes in the final overmolded material.

A few portions of the rigid housing are exposed on the top surface of the final sensor shown in FIG. 1A. This includes the curvilinear alignment groove 28, as well as a light emitter window 36 and a light detector window 38. These windows are preferably formed of a clear thermoplastic which is injection-molded into the remainder of housing 12 before the addition of components and the overmolding process. Housing 12 is preferably an opaque or black thermoplastic.

Also shown are a pair of contact electrodes 40, which are electrically tied together, and can be used in conjunction with another contact electrode 42 to determine when the sensor is down on the skin of a fetus. These contact electrodes provide a current between electrodes 40 and 42 which flows through the fluid inside the uterus, with the fluid contact path being disrupted when the sensor is down on the fetus' skin, changing the impedance and allowing a detection of the sensor being properly placed. Electrode 42 is recessed within groove 28 in order to allow it be in contact with the amniotic fluid, which can flow through the groove. Thus, the groove conveniently serves two purposes, allowing the amniotic fluid to reach electrode 42 and also provides an anchoring mechanism for keeping the housing 12 from slipping during the injection-molding process. In an alternate embodiment, contact electrode 42 could be placed anywhere on the sensor surface where it would contact the amniotic fluid.

In operation, the sensor of FIGS. 1A and 1B is inserted into the mother's vagina and must be flexible enough to bend around between the fetus and the inside of the cervical and/or uterine walls. The preformed, bent portion 46 of the sensor is designed to apply pressure against the mother's cervical or uterine wall to force the face of the sensor having the emitter and detector windows 38 and 36 against the fetus.

FIG. 2 illustrates the assembly of the components into housing 12 prior to being overmolded. The view in FIG. 2 is the backside, or the opposite of the side shown in FIG. 1A. Housing 12 is preferably made of an injection-molded thermoplastic which is opaque or black. Over this, transparent injection-molded plastic windows 38 and 36 are formed on the top end (the bottom as shown in FIG. 2) of detector enclosure 48 and emitter enclosure 50, respectively. As can be seen, housing 12 is wide in the lateral direction, providing lateral stiffness to the sensor.

A light emitter package 52 is inserted into enclosure 50, bonded to twisted pair wire leads 54. Once inside the enclosure, a lid 56 is placed over the backside of enclosure 52 to keep out the overmolding material during the injection-molding process. This prevents the overmolding Santoprene™ from getting around the edges of emitter 52 and blocking the light emission on the other side through window 36.

A photodetector module 58 is placed into enclosure 48 and similarly covered by a lid 60. Detector module 58 is connected to twisted pair wires 62. The assembly of detector module 58 is shown in more detail in FIGS. 3 and 4, discussed below. In one embodiment, cap or lids 56 and 60 are held in place by staking the top edges of enclosures 50 and 48, which extend slightly beyond where the lid would be placed in order to allow such staking. The staking can be done with the use of heat, sonic or ultrasonic sound or pressure, or any combination, in order to slightly spread the edges of the enclosure to hold the lids in place. Alternately, castellations could be used similar to those used to hold the wires in place.

Also shown in FIG. 2 are contact electrodes 40 which are inserted through holes 64, and electrode 42 which is inserted through a hole 66. Contact electrodes 40 are pressfit through the holes to provide a secure, sealed attachment. Electrodes 40 may optionally include ribs or ringed barbs to increase their surface area and help retain them in holes 64.

Figure 5:
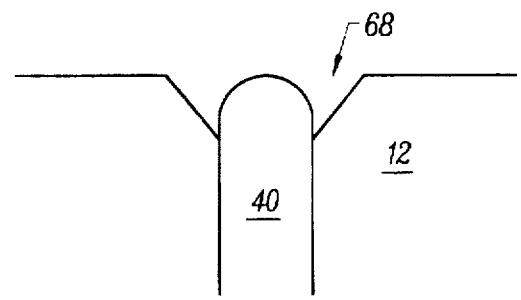
FIG. 5 is a diagram illustrating a side view of the press-fit opening for the contact electrode in the present invention.

Turning briefly to FIG. 5, this shows the other end of an electrode 40 extending out of a hole 64 of housing 12. As can be seen, there is a tapered or crater-like opening 68 which exposes the tip and a portion of the sides of contact electrode 40. The contact pin has a rounded end, so that it will not scratch the fetus. However, if the end of the contact end was level with the housing, vernix and other solids encountered in the uterine environment would tend to cover and impede the operation of the electrode. The use of a crater or tapered opening 68 provides the maximum exposed contact area to improve chances of fluid contact in case of insulating substances. In order to keep Santoprene™ from filling this crater during overmolding, the portion of housing 12 around these contact electrodes extends to the surface of the sensor, and contacts the top of the mold.

Returning to FIG. 2, housing 12 includes a number of castellations 70 around its perimeter. These castellations are so-called because they resemble the castellations on a castle wall in their shape and location. Between castellations 70 and the interior portions of the housing, is a pathway in which the wires can be placed, for example in grooves 72 and 74. Once the wires are in place, castellations 70 can be bent slightly inward to hold the wires in place. In bending castellations, ultrasonic, sonic or heat could be used to aid in the bending process. The remaining components, such as the lids and the electrodes, are held in place by press-fits.

A cap 76 is provided with a pair of openings 78 which fit over protrusions 80 on housing 12. Wings 82 fit around the sides of a cable jacket 84. A formed recess 86 at the end of cap 76 provides a cavity into which a stylet can be inserted. A stylet is typically inserted through cable jacket 84 from an exterior point to add stiffness to the cable during insertion of the cable and sensor into the mother's vagina. Enclosure 86 provides a hard stop for the stylet to ensure that it does not go any further and damage portions of the sensor by penetrating the flexible, overmolded material.

The twisted pair wires of FIG. 2 are shown covered by braided wire mesh 88. To keep the mesh from untangling near the far end, an ultra-thin heat shrink tubing 90 is used to prevent the fraying of these braided wire shields. The thin tape tubing enables the shields to be held in place without making the resulting wire thickness so large that it is difficult to fit into the rest of the assembly. The braided wire shields are grounded and used for shielding from electromagnetic radiation which would interfere with the signals along the twisted pair wire. Twisted pairs are used to further decrease electromagnetic interference.

Housing 12 also includes a pair of lateral extending wings 92 which extend to the sides of the mold during the overmolding process to register the housing to the mold and maintain a proper alignment of housing 12 during the overmolding process. Alternately, any other feature could be used to maintain lateral alignment, such as feature extending from the mold rather than from the housing. Once the components shown in FIG. 2 are loaded into and secured to housing 12, the housing is placed into a mold and overmolding is accomplished by injecting Santoprene™ through an opening at position 32, as shown in FIG. 1B. The overmolding material flows down through the mold to cover the housing and components, except where prevented, and also to cover the connection to cable jacket 84.

Referring again to FIG. 2, there is an opening 81 into detector enclosure 48, and openings 83 into emitter enclosure 50 to allow access for the twisted pair wires. These openings, which become holes when the lids are placed on them, are small enough to allow the conducting wires to feed through, but are tight enough to prevent the Santoprene™ overmolding material from entering the cavities. These openings are also not in the direct flow path, further limiting Santoprene™ from entering. The detector opening is opposite the flow direction, while the emitter openings are recessed.

Figure 3:
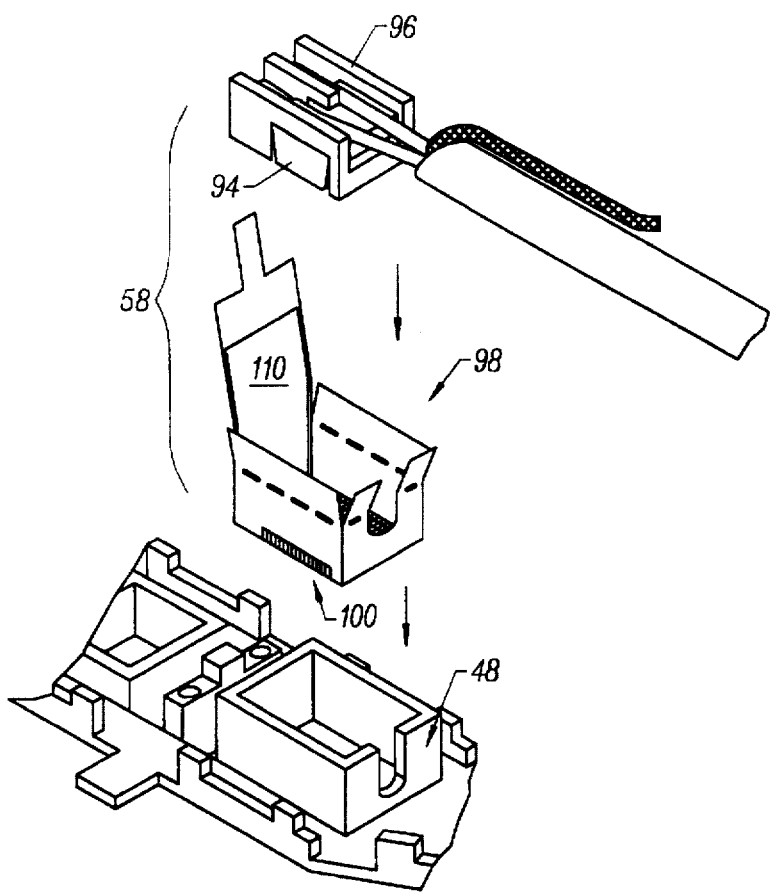
FIG. 3 is a diagram illustrating the assembly of the detector block module.

FIG. 3 illustrates the assembly of detector block 58 shown in FIG. 2. Detector block 58 consists of an integrated circuit photodetector 94 mounted in a detector block 96. Block 96 is used because a typical, photodetector IC 94 is irregularly shaped, so that it would not fit snugly into a rectangular enclosure, and is difficult to cover with a Faraday shield. Accordingly, block 96 provides an opening into which the photodetector 94 can be inserted, as well as providing surfaces along different edges of a rectangular block for supporting a Faraday shield.

A Faraday shield 98 is provided, with a screen portion 100 covering the face of the detector pointing outward through the clear window 38 of FIG. 2. The screen serves to prevent electromagnetic interference with the signals generated by the photodetector, so that the signals generated are purely as a result of detected light. The Faraday shield is shaped so that it will fold like a box around the detector block 96.

Figure 4:
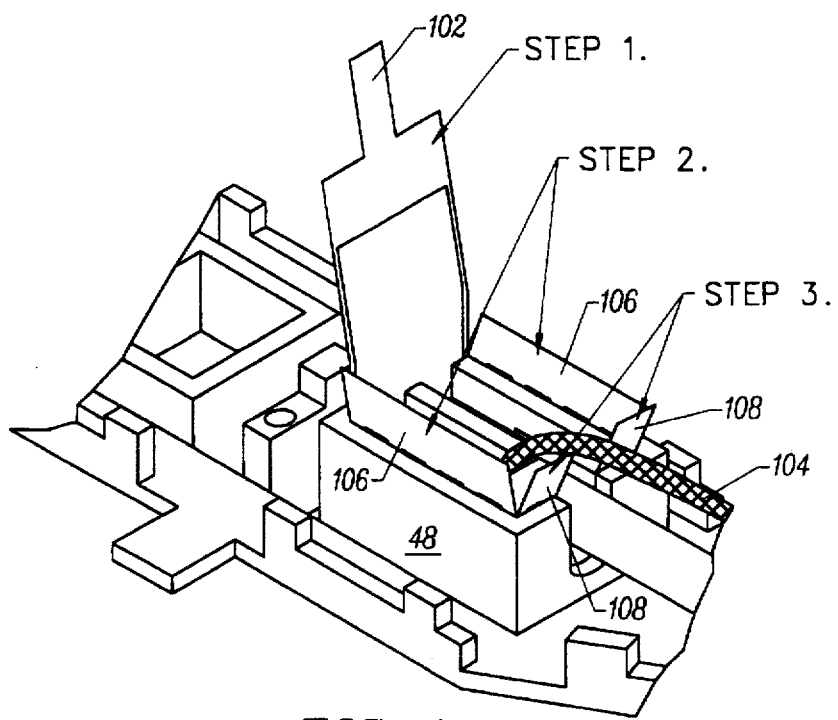
FIG. 4 is a diagram illustrating an inserted detector block module.

FIG. 4 shows the detector assembly inserted into the detector enclosure 48, after which the edges of the Faraday shield are folded over as illustrated. First, the top end is folded over so that a tab 102 extends outside enclosure 48 where it can be connected to the wire braid ground shield 104. Subsequently, tabs 106 are folded over, followed by tabs 108 being folded over to complete the enclosure, with the folds overlapping. Thus, the Faraday shield provides a screen 100 on one side, while enclosing the rest of the detector module with a conducting ground plane. Non-conducting tape 110 is placed on the inside surface of the shield to prevent shorting with the ground connection to the wire connections connected to the photodetector chip. After assembly, the lid 60 shown in FIG. 2 is then placed on top of detector module 58 to seal off the backside of detector enclosure 48. The inside of the Faraday shield is preferably reflective, and the detector block is transparent, to maximize the light which is captured by the detector.

The method of assembly in the present invention minimizes the need for any taping, soldering or other labor-intensive actions. Instead, press-fits are used, such as for the electrodes and the lids, along with a folding design for the Faraday cage which is held in place by a press-fit lid. These features provide for an easily assembled housing, and also provide for a watertight assembly through the use of such press-fits.

Figure 6:
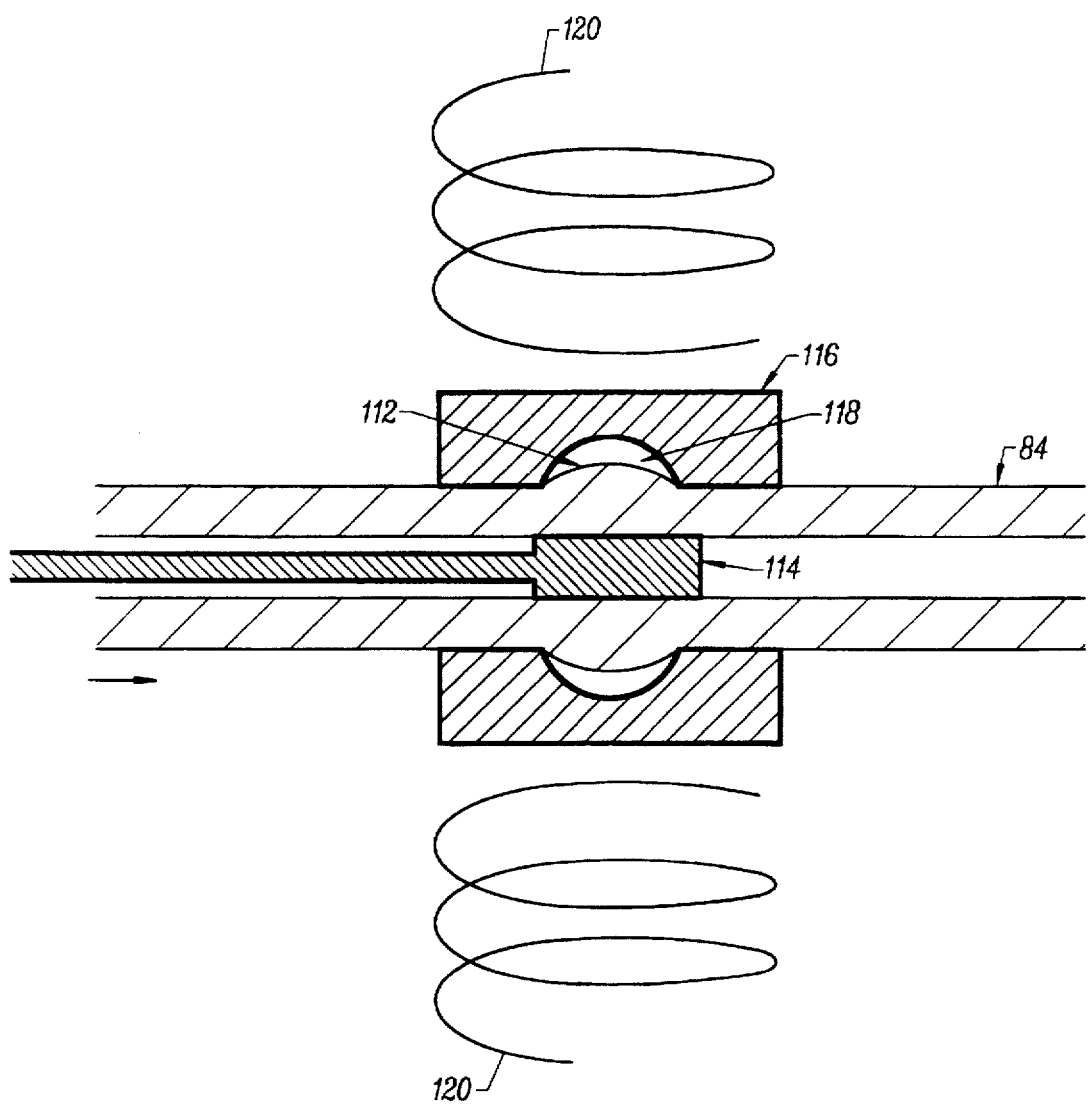
FIG. 6 is a diagram illustrating the process for forming a tactile bump on a cable according to the present invention.

FIG. 6 illustrates the formation of a tactile bump 112 on a portion of cable 84. This bump is typically formed a short distance from the sensor so that a clinician can insert the sensor and, by feeling the bump, know how far the sensor has been inserted. The formation of the bump is accomplished with a mandrel 114 having a cross-section matching the cable jacket cavity which is inserted into the hollow cable 84. Mandrel 114 is made of metal, so that it will heat upon the application of an electromagnetic field. A Teflon™ mold 116 surrounds the cable at the position of the mandrel block 114, with a cavity 118 defining the shape of the desired final tactile bump. Wire coil 120 is positioned to generate an inductive electromagnetic field, which will heat up mandrel block 114, thereby softening the portion of cable 84 adjacent it and forcing it into cavity 118 of the Teflon™ mold 116. Since the mold is made of Teflon™ it will not separately be heated by induction, and is resistant to heat, with the heat thus being generated from the inside out. The technique of a metal mandrel and a Teflon™ mold has been used to seal the ends of cables in the prior art. Here, this technique is uniquely applied to generating a tactile bump in the middle of a cable. Alternatively, the tactile feature could be a dent or other shape.

Cable 84 of FIG. 6 is a cable jacket, which is manufactured by extrusion before having the tactile bump formed.

After the tactile bump is formed as shown in FIG. 6, the wires are threaded through the cable jacket and connected to the housing components as shown in FIG. 2. An opening in the cable jacket on the order of a foot or so from the sensor is used for the insertion of a stylet to stiffen the cable for insertion. After insertion and appropriate placement of the sensor on a fetus, the stylet can be removed.

Although certain embodiments of the invention have been shown, other embodiments may be used to realize the present invention, the scope of which is set forth in the appended claims. For example, molding techniques other than injection-molding might be used, and materials other than plastic might be used for the housing. For instance, the housing could be made of thermo-sets, such as silicones, epoxies, polyester, or other thermoplastics, such as nylon, PVC, polyurethane or a fiberglass. The materials are preferably chosen, however, so that the overmolding material will bond to the housing material. In another example, although castellations are shown for holding the wires in place, snap fits or other securing mechanisms could be used. Additionally, although the embodiments of the present invention have been discussed in connection with a fetal sensor, the present invention could also be used on sensors used for adults or children where a flexible sensor is desired.

What is claimed is:

1. An oximeter sensor comprising:
   a housing formed from a material with a first rigidity;
   a plurality of oximeter components mounted in said housing, including at least a light source and a light detector;
   an overmolded material covering most of said housing on multiple sides of said housing, leaving openings to expose at least said light source and said light detector, said overmolding material having a second rigidity which is less than said first rigidity.

2. The sensor of claim 1 wherein said housing is made of plastic and said overmolded material is an injection molded thermoplastic elastomer.

3. The sensor of claim 2 wherein said housing is made of polypropylene.

4. The sensor of claim 1 wherein said housing has at least portions which are thinner in a Z direction than a dimension of said housing in an X direction, such that the combination of said first housing and said overmolded material is flexible to bend in the Z direction.

5. The sensor of claim 1 wherein said sensor is a fetal sensor.

6. The sensor of claim 1 wherein said oximeter sensor is a pulse oximeter sensor.

7. The sensor of claim 1 wherein said light source and light detector are mounted at positions effective for reflectance oximetry.

8. The sensor of claim 1 further comprising:
   a plurality of contact electrodes;
   a plurality of lines connecting said contact electrodes to said oximeter components; and
   an opening in said housing having a size to provide a press-fit for one of said contact electrodes.

9. The sensor of claim 8 wherein said opening is flared at an exposed surface, exposing a portion of a side of each of said plurality of contact electrodes.

10. The sensor of claim 1 further comprising:
    a plurality of wires extending along said housing and connected to said oximeter components; and
    a plurality of castellations extending from said housing and bent over said wires to secure said wires.

11. The sensor of claim 1 further comprising:
    a feature in said housing for mating with a feature in a mold to hold said housing in place against a longitudinal stream of injected overmolding material.

12. The sensor of claim 11 wherein said feature in said housing comprises a curved groove in said housing.

13. The sensor of claim 1 further comprising at least one feature of said housing for registering said housing in a mold to insure proper lateral alignment of said housing during an injection of overmolding material.

14. The sensor of claim 13 wherein said feature of said housing is a pair of wings extending from sides of said housing.

15. The sensor of claim 1 further comprising at least one stand-off feature of said housing on the same side as said openings to insure coverage of said side of said housing by said overmolding material.

16. The sensor of claim 1 further comprising:
    a cable attached to a first end of said housing; and
    a rigid cap mounted to said housing adjacent said first end of said housing, said cap having a recess shaped to receive the end of a stylet inserted through said cable.

17. The sensor of claim 1 further comprising:
    a rectangular block having a void for receiving said detector; and
    an enclosure in said housing for receiving said detector block.

18. The sensor of claim 17 further comprising a Faraday shield shaped to fold around said rectangular block, and held in place by a press fit between said rectangular block and said enclosure.

19. The sensor of claim 1 further comprising:
    a pair of enclosures in said housing for receiving said light source and said light detector, respectively; and
    a pair of lids for covering said enclosures to seal said emitter and detector from said overmolding material.

20. The sensor of claim 1 further comprising:
    a plurality of wires connected to said oximeter components;
    at least one braided wire shield covering at least one of said wires; and
    a thin heat shrink tubing around an end of said braided wire shield.

21. The oximeter sensor of claim 1 further comprising an injection molded clear plastic covering said openings, and wherein said housing and said overmold material are opaque.

22. An oximeter sensor comprising:
    a housing having at least portions which are thinner in a Z direction than a dimension of said housing in an X direction, such that the combination of said first housing and said overmolded material is flexible to bend away from a Y axis, said housing being made of a material of a first rigidity;
    a plurality of oximeter components mounted in said housing, including at least a light source and a light detector; and
    an overmolded material covering portions of said housing, said overmolded material being of a lesser rigidity than said housing.

23. The oximeter sensor of claim 22 further comprising a plurality of alignment features for aligning said housing in a mold during an overmolding process.

24. The sensor of claim 23 wherein one of said alignment features comprises:

a curved groove in said housing for mating with a corresponding groove in a mold to hold said housing in place against a longitudinal stream of injected overmolding material.

25. The sensor of claim 23 wherein one of said alignment features comprises a pair of wings extending from sides of said housing for registering said housing in a mold during an injection of overmolding material.

26. The sensor of claim 23 wherein one of said alignment features comprises at least one stand-off protrusion extending from said housing on the same side as said openings to insure coverage of said side of said housing by said overmolding material.

27. The sensor of claim 22, wherein said sensor is a fetal pulse oximeter sensor with said light source and light detector positioned for reflectance oximetry.

28. The sensor of claim 22 further comprising means for securing said oximeter components in proper alignment during an overmolding process.

29. The sensor of claim 28 further comprising:
a plurality of wires extending along said housing and connected to said oximeter components; and
said means for securing including a plurality of castellations extending from said housing and bent over said wires to secure said wires.

30. The sensor of claim 28 wherein said means for securing comprises:
a rectangular block having a void for receiving said detector; and
an enclosure in said housing for receiving said detector block.

31. The sensor of claim 30 further comprising a Faraday shield shaped to fold around said rectangular block, and held in place by a press fit between said rectangular block and said enclosure.

32. The sensor of claim 28 wherein said means for securing comprises:
a pair of enclosures in said first housing for receiving said light source and said light detector, respectively; and
a pair of lids for covering said enclosures to seal said emitter and detector from said overmolding material.

33. The sensor of claim 22 wherein said housing is made of plastic and said overmolded material is an injection molded thermoplastic elastomer.

34. The sensor of claim 33 wherein said housing is made of polypropylene.

35. The sensor of claim 22 further comprising:
a plurality of contact electrodes;
a plurality of lines connecting said contact electrodes to said oximeter components, and
an opening in said housing having a size to provide a press-fit for one of said contact electrodes.

36. The sensor of claim 35 wherein said opening is flared at an exposed surface, exposing a portion of a side of each of said plurality of contact electrodes.

37. The sensor of claim 22 further comprising:
a cable attached to a first end of said housing; and
a rigid cap mounted to said housing adjacent said first end of said housing, said cap having a recess shaped to receive the end of a stylet inserted through said cable.

38. The sensor of claim 22 further comprising:
a plurality of wires connected to said oximeter components;
at least one braided wire shield covering at least one of said wires; and
a thin heat shrink tubing around an end of said braided wire shield.

39. The oximeter sensor of claim 22 further comprising an injection molded clear plastic covering said openings, and wherein said housing and said overmold material are opaque.

40. A fetal pulse oximeter reflectance sensor comprising:
a housing having at least portions which are thinner in a Z direction than a dimension of said housing in an X direction, such that the combination of said first housing and said overmolded material is flexible to bend away from a Y axis, said housing being made of a material of a first rigidity;
a plurality of oximeter components mounted in said housing, including at least a light source and a light detector;
an overmolded material covering portions of said housing, said overmolded material being of a lesser rigidity than said housing;
a plurality of alignment features for aligning said housing in a mold during an overmolding process;
means for securing said oximeter components in proper alignment during an overmolding process; and
wherein said housing is made of plastic and said overmolded material is an injection molded thermoplastic elastomer.

41. An oximeter sensor comprising:
a housing;
a plurality of oximeter components mounted in said housing, including at least a light source and a light detector;
an overmolded material covering most of said housing on multiple sides of said housing, leaving openings to expose at least said light source and said light detector; and
said components being located adjacent a neutral axis of the combination of said housing and said overmolded material;
wherein said housing is made of a material of a first rigidity and said overmolded material is made of a material of a second rigidity which is less than said first rigidity.

* * * * *